(12) United States Patent
Fischer et al.

(10) Patent No.: US 7,795,303 B2
(45) Date of Patent: Sep. 14, 2010

(54) ACTIVE AGENTS COMBINATION EXHIBITING INSECTICIDAL AND ACARICIDE PROPERTIES

(75) Inventors: Reiner Fischer, Monheim (DE); Thomas Bretschneider, Lohmar (DE); Rüdiger Fischer, Pulheim (DE); Christian Funke, Leichlingen (DE); Wolfgang Thielert, Odenthal (DE)

(73) Assignee: Bayer CropScience AG, Monheim (DE)

( * ) Notice: Subject to any disclaimer, the term of this patent is extended or adjusted under 35 U.S.C. 154(b) by 1157 days.

(21) Appl. No.: 10/563,205

(22) PCT Filed: Jun. 25, 2004

(86) PCT No.: PCT/EP2004/006913

§ 371 (c)(1),
(2), (4) Date: May 15, 2006

(87) PCT Pub. No.: WO2005/004604

PCT Pub. Date: Jan. 20, 2005

(65) Prior Publication Data

US 2007/0142463 A1  Jun. 21, 2007

(30) Foreign Application Priority Data

Jul. 8, 2003  (DE)  ................................ 103 30 723

(51) Int. Cl.
  *A01N 43/08* (2006.01)
  *A01N 43/12* (2006.01)
  *A01N 37/30* (2006.01)
  *A01N 37/18* (2006.01)
(52) U.S. Cl. ...................................... 514/462; 514/616
(58) Field of Classification Search ................. 514/462, 514/616
  See application file for complete search history.

(56) References Cited

U.S. PATENT DOCUMENTS

| | | | |
|---|---|---|---|
| 3,264,177 A | 8/1966 | Kenaga | 167/30 |
| 4,053,634 A | 10/1977 | Bellina et al. | 424/312 |
| 4,055,661 A | 10/1977 | Bellina et al. | 424/311 |
| 4,070,481 A | 1/1978 | Bellina et al. | 424/311 |
| 4,082,848 A | 4/1978 | Bellina et al. | 424/273 R |
| 4,115,584 A | 9/1978 | Bellina et al. | 424/301 |
| 4,148,918 A | 4/1979 | Bellina et al. | 424/314 |
| 4,843,068 A | 6/1989 | Hamaguchi et al. | 514/63 |
| 4,962,126 A | 10/1990 | Drabek | 514/587 |
| 5,010,098 A | 4/1991 | Brown et al. | 514/426 |
| 5,262,383 A * | 11/1993 | Fischer et al. | 504/195 |
| 5,367,093 A | 11/1994 | Dekeyser et al. | 560/27 |
| 5,438,123 A | 8/1995 | Dekeyser et al. | 534/885 |
| 5,455,263 A | 10/1995 | Doscher et al. | 514/422 |
| 5,478,855 A | 12/1995 | Suzuki et al. | 514/374 |
| 5,536,746 A | 7/1996 | Dekeyser et al. | 514/468 |
| 5,610,122 A | 3/1997 | Fischer et al. | 504/251 |
| 5,719,310 A | 2/1998 | Fischer et al. | 560/83 |
| 5,830,825 A | 11/1998 | Fischer et al. | 504/130 |
| 5,945,444 A | 8/1999 | Fischer et al. | 514/445 |
| 5,994,274 A | 11/1999 | Fischer et al. | 504/282 |
| 6,051,723 A | 4/2000 | Fischer et al. | 549/420 |
| 6,110,872 A | 8/2000 | Lieb et al. | 504/284 |
| 6,114,374 A | 9/2000 | Lieb et al. | 514/424 |
| 6,140,358 A | 10/2000 | Lieb et al. | 514/425 |
| 6,251,830 B1 | 6/2001 | Fischer et al. | 504/251 |
| 6,255,342 B1 | 7/2001 | Lieb et al. | 514/533 |
| 6,271,180 B2 | 8/2001 | Lieb et al. | 504/292 |
| 6,288,102 B1 | 9/2001 | Hagemann et al. | 514/409 |
| 6,316,486 B1 | 11/2001 | Lieb et al. | 514/411 |
| 6,358,887 B1 | 3/2002 | Fischer et al. | 504/284 |
| 6,359,151 B2 | 3/2002 | Lieb et al. | 549/265 |
| 6,362,369 B2 | 3/2002 | Tohnishi et al. | 564/156 |
| 6,380,246 B1 | 4/2002 | Lieb et al. | 514/462 |
| 6,388,123 B1 | 5/2002 | Lieb et al. | 560/76 |
| 6,391,912 B1 | 5/2002 | Hagemann et al. | 514/444 |
| 6,417,370 B1 | 7/2002 | Lieb et al. | 548/408 |
| 6,451,843 B1 | 9/2002 | Lieb et al. | 514/422 |
| 6,458,965 B1 | 10/2002 | Lieb et al. | 548/408 |
| 6,469,196 B2 | 10/2002 | Fischer et al. | 560/105 |
| 6,486,343 B1 | 11/2002 | Lieb et al. | 560/39 |
| 6,504,036 B1 | 1/2003 | Lieb et al. | 549/265 |
| 6,511,942 B1 | 1/2003 | Lieb et al. | 504/299 |
| 6,559,341 B2 | 5/2003 | Tohnishi et al. | 564/442 |
| 6,589,976 B1 | 7/2003 | Fischer et al. | 514/409 |
| 6,596,873 B1 | 7/2003 | Lieb et al. | 546/256 |
| 6,603,044 B1 | 8/2003 | Tohnishi et al. | 564/154 |
| 6,630,594 B2 | 10/2003 | Hagemann et al. | 548/410 |
| 6,642,379 B1 | 11/2003 | Furuya et al. | 544/88 |

(Continued)

FOREIGN PATENT DOCUMENTS

| | | | |
|---|---|---|---|
| DE | 199 39 395 A | | 4/2004 |
| EP | 0 528 156 A | | 2/1993 |
| EP | 1 380 209 A | | 1/2004 |
| JP | 2001-335559 | | 12/2001 |

(Continued)

OTHER PUBLICATIONS

Chem. Ind. 37, (month unavailable) 1985, pp. 730-732, Harry R. Ungerer, "Schiffsfarben—eine Spezialität der seenahen Lackindustire".

Weeds, 15, (month unavailable) 1967, pp. 20-22, S.R. Colby, "Calculating Synergistic and Antagonistic Responses of Herbicide Combinations".

*Primary Examiner*—John Pak
(74) *Attorney, Agent, or Firm*—Richard E. L. Henderson

(57) ABSTRACT

The present invention relates to novel active compound combinations of cyclic ketoenols of the formula (I) and active compounds of the formula (II) detailed in the disclosure having very good insecticidal and acaricidal properties.

3 Claims, No Drawings

U.S. PATENT DOCUMENTS

| | | | |
|---|---|---|---|
| 6,693,092 B2 | 2/2004 | Lieb et al. | 514/183 |
| 6,716,832 B2 | 4/2004 | Lieb et al. | 514/183 |
| 6,746,990 B2 | 6/2004 | Fischer et al. | 504/299 |
| 6,747,041 B1 | 6/2004 | Katsuhira et al. | 514/307 |
| 6,759,548 B2 | 7/2004 | Fischer et al. | 560/81 |
| 6,806,264 B2 | 10/2004 | Lieb et al. | 514/183 |
| 6,835,847 B2 | 12/2004 | Bretschneider et al. | 556/419 |
| 6,858,741 B2 | 2/2005 | Lieb et al. | 549/67 |
| 6,861,391 B1 | 3/2005 | Fischer et al. | 504/283 |
| 6,864,289 B1 | 3/2005 | Tohnishi et al. | 514/617 |
| 6,875,768 B1 | 4/2005 | Machiya et al. | 514/256 |
| 6,933,261 B2 | 8/2005 | Lieb et al. | 504/298 |
| 2001/0004629 A1 | 6/2001 | Lieb et al. | 504/292 |
| 2001/0041814 A1 | 11/2001 | Tohnishi et al. | 564/156 |
| 2002/0010204 A1 | 1/2002 | Lieb et al. | 514/424 |
| 2002/0022575 A1 | 2/2002 | Fischer et al. | 504/221 |
| 2002/0072617 A1 | 6/2002 | Hagemann et al. | 548/541 |
| 2002/0161034 A1 | 10/2002 | Hagemann et al. | 514/432 |
| 2002/0188136 A1 | 12/2002 | Lieb et al. | 548/368.4 |
| 2003/0045432 A1 | 3/2003 | Fischer et al. | 504/221 |
| 2003/0055287 A1 | 3/2003 | Tohnishi et al. | 564/154 |
| 2003/0073851 A1 | 4/2003 | Lieb et al. | 548/366.4 |
| 2003/0096806 A1 | 5/2003 | Lieb et al. | 514/212.01 |
| 2003/0100604 A1* | 5/2003 | Fischer et al. | 514/473 |
| 2003/0114312 A1* | 6/2003 | Fischer et al. | 504/299 |
| 2003/0144504 A1 | 7/2003 | Fischer et al. | 544/54 |
| 2003/0171219 A1 | 9/2003 | Lieb et al. | 504/221 |
| 2003/0216260 A1 | 11/2003 | Ruther et al. | 504/283 |
| 2004/0009982 A1 | 1/2004 | Tohnishi et al. | 514/247 |
| 2004/0077500 A1 | 4/2004 | Sakata et al. | 504/261 |
| 2004/0077597 A1 | 4/2004 | Bretschneider et al. | 514/63 |
| 2004/0097595 A1 | 5/2004 | Nakao et al. | 514/616 |
| 2004/0116299 A1 | 6/2004 | Harayama et al. | 504/335 |
| 2004/0127365 A1 | 7/2004 | Lieb et al. | 504/282 |
| 2004/0152598 A1 | 8/2004 | Goto et al. | 504/270 |
| 2004/0167031 A1 | 8/2004 | Lieb et al. | 504/308 |
| 2005/0038021 A1 | 2/2005 | Lieb et al. | 514/227.5 |
| 2005/0164885 A1 | 7/2005 | Lieb et al. | 504/221 |

FOREIGN PATENT DOCUMENTS

| | | |
|---|---|---|
| WO | 00/56156 A | 9/2000 |
| WO | 02/087334 A | 11/2002 |
| WO | 02/094766 | 11/2002 |
| WO | 2004/034786 A | 4/2004 |

* cited by examiner

ACTIVE AGENTS COMBINATION EXHIBITING INSECTICIDAL AND ACARICIDE PROPERTIES

The present patent application has been filed under 35 U.S.C. 371 as a national stage application of PCT/EP2004/006913, filed Jun. 25, 2004, which was published in German as International Patent Publication WO 2005/004604 on Jan. 20, 2005, and is entitled to the right of priority of German Patent Application 103 30 723.0, filed Jul. 8, 2003.

The present invention relates to novel active compound combinations comprising both known cyclic ketoenols and further known insecticidally active compounds, which combinations are highly suitable for controlling animal pests, such as insects and unwanted acarids.

It is already known that cyclic ketoenols have fungicidal, insecticidal and acaricidal properties (EP-A-528 156, EP-A-0 647 637, WO 95/26 345, WO 96/20 196, WO 96/25 395, WO 96/35 664, WO 97/01 535, WO 97/02 243, WO 97/36 868, WO 98/05 638, WO 98/25 928, WO 99/16 748, WO 99/43 649, WO 99/48 869, WO 99/55 673, WO 01/23 354 and WO 01/74 770). The activity of these compounds is good; however, at low application rates it is sometimes unsatisfactory.

It is also known that mixtures of phthalic diamides and further bioactive compounds have insecticidal and/or acaricidal action (WO 02/087 334). However, the action of these mixtures is not always optimal.

Furthermore, it is already known that numerous heterocycles, organotin compounds, benzoylureas and pyrethroids have insecticidal and acaricidal properties (cf. WO 93-22 297, WO 93-10 083, DE-A 2 641 343, EP-A-347 488, EP-A-210 487, U.S. Pat. No. 3,264,177 and EP-A-234 045). However, the action of these compounds is not always satisfactory.

It has now been found that compounds of the formula (I)

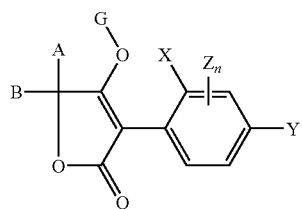

(I)

in which

X represents $C_1$-$C_6$-alkyl, bromine, $C_1$-$C_6$-alkoxy or $C_1$-$C_3$-haloalkyl, Y represents hydrogen, $C_1$-$C_6$-alkyl, halogen, $C_1$-$C_6$-alkoxy, $C_1$-$C_3$-haloalkyl, Z represents $C_1$-$C_6$-alkyl, halogen, $C_1$-$C_6$-alkoxy, n represents a number from 0 to 3, A represents hydrogen or in each case optionally halogen-susbituted straight-chain or branched $C_1$-$C_{12}$-alkyl, $C_2$-$C_8$-alkenyl, $C_2$-$C_8$-alkynyl, $C_1$-$C_{10}$-alkoxy-$C_1$-$C_8$-alkyl, $C_1$-$C_8$-polyalkoxy-$C_2$-$C_8$-alkyl, $C_1$-$C_{10}$-alkylthio-$C_2$-$C_8$-alkyl, cycloalkyl having 3 to 8 ring atoms which may be interrupted by oxygen and/or sulphur or represents in each case optionally halogen-, $C_1$-$C_6$-alkyl-, $C_1$-$C_6$-haloalkyl-, $C_1$-$C_6$-alkoxy-, $C_1$-$C_6$-haloalkoxy-, nitro-substituted phenyl or phenyl-$C_1$-$C_6$-alkyl, B represents hydrogen, $C_1$-$C_6$-alkyl or $C_1$-$C_6$-alkoxy-$C_1$-$C_4$-alkyl or in which A and B together with the carbon atom to which they are attached form a saturated or unsaturated 3- to 8-membered ring which is optionally interrupted by oxygen and/or sulphur and optionally substituted by halogen, $C_1$-$C_6$-alkyl, $C_1$-$C_6$-alkoxy, $C_1$-$C_4$-haloalkyl, $C_1$-$C_4$-haloalkoxy, $C_1$-$C_4$-alkylthio or optionally substituted phenyl or is optionally benzofused, G represents hydrogen (a) or represents a group

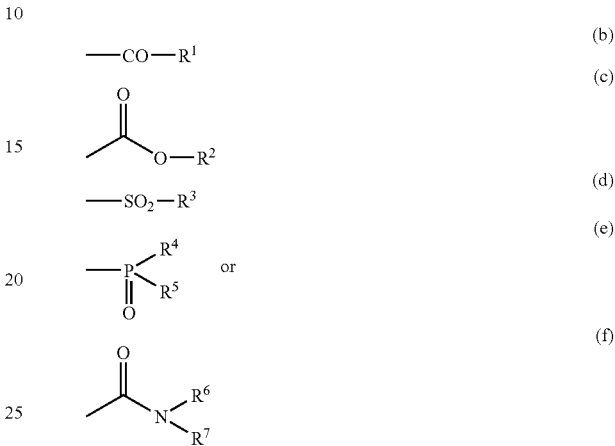

in which $R^1$ represents in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, $C_1$-$C_8$-polyalkoxy-$C_2$-$C_8$-alkyl or cycloalkyl having 3 to 8 ring atoms which may be interrupted by oxygen and/or sulphur atoms, represents optionally halogen-, nitro-, $C_1$-$C_6$-alkyl-, $C_1$-$C_6$-alkoxy-, $C_1$-$C_6$-haloalkyl-, $C_1$-$C_6$-haloalkoxy-substituted phenyl;

represents optionally halogen-, $C_1$-$C_6$-alkyl-, $C_1$-$C_6$-alkoxy-, $C_1$-$C_6$-haloalkyl-, $C_1$-$C_6$-haloalkoxy-substituted phenyl-$C_1$-$C_6$-alkyl, represents in each case optionally halogen- and/or $C_1$-$C_6$-alkyl-substituted pyridyl, pyrimidyl, thiazolyl or pyrazolyl, represents optionally halogen- and/or $C_1$-$C_6$-alkyl-substituted phenoxy-$C_1$-$C_6$-alkyl, $R^2$ represents in each case optionally halogen-substituted $C_1$-$C_{20}$-alkyl, $C_2$-$C_{20}$-alkenyl, $C_1$-$C_8$-alkoxy-$C_2$-$C_8$-alkyl or $C_1$-$C_8$-polyalkoxy-$C_2$-$C_8$-alkyl, represents in each case optionally halogen-, nitro-, $C_1$-$C_6$-alkyl-, $C_1$-$C_6$-alkoxy-, $C_1$-$C_6$-haloalkyl-substituted phenyl or benzyl, $R^3$ represents optionally halogen-substituted $C_1$-$C_8$-alkyl, represents in each case optionally $C_1$-$C_4$-alkyl-, halogen-, $C_1$-$C_4$-haloalkyl-, $C_1$-$C_4$-alkoxy-, $C_1$-$C_4$-haloalkoxy-, nitro- or cyano-substituted phenyl or benzyl, $R^4$ and $R^5$ independently of one another represent in each case optionally halogen-substituted $C_1$-$C_8$-alkyl, $C_1$-$C_8$-alkoxy, $C_1$-$C_8$-alkylamino, di-($C_1$-$C_8$)alkylamino, $C_1$-$C_8$-alkylthio, $C_2$-$C_5$-alkenylthio, $C_2$-$C_5$-alkynylthio, $C_3$-$C_7$-cycloalkylthio, represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl-, $C_1$-$C_4$-haloalkyl-substituted phenyl, phenoxy or phenylthio, $R^6$ and $R^7$ independently of one another represent in each case optionally halogen-substituted $C_1$-$C_{10}$-alkyl, $C_1$-$C_{10}$-alkoxy, $C_3$-$C_8$-alkenyl, $C_1$-$C_8$-alkoxy-$C_1$-$C_8$-alkyl, represent optionally halogen-, $C_1$-$C_6$-haloalkyl-, $C_1$-$C_6$-alkyl- or $C_1$-$C_6$-alkoxy-substituted phenyl, represent optionally halogen-, $C_1$-$C_6$-alkyl-, $C_1$-$C_6$-haloalkyl- or $C_1$-$C_6$-alkoxy-substituted benzyl or together represent a 5- or 6-membered ring which is optionally interrupted by oxygen or sulphur and which may optionally be substituted by $C_1$-$C_6$-alkyl, and at least one phthalic diamide of the formula (II) are synergistically active and suitable for controlling animal pests.

The phthalic diamides of the formula (II) are likewise known compounds which are known or embraced by the following publications (cf. EP-A-0 919 542, EP-A-1 006 107, WO 01/00 575, WO 01/00 599, WO 01/46 124, JP 2001-33 555 9, WO 01/02354, WO 01/21 576, WO 02/08 8074, WO 02/08 8075, WO 02/09 4765, WO 02/09 4766, WO 02/06 2807).

The generic formulae and definitions described in these publications and the individual compounds described therein are expressly incorporated herein by way of reference.

The phthalic diamides can be summarized by formula (II):

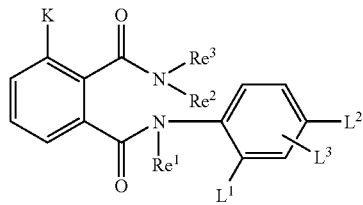

(II)

in which

K represents halogen, cyano, alkyl, haloalkyl, alkoxy or haloalkoxy, $Re^1$, $Re^2$, $Re^3$ each independently of one another represent hydrogen, cyano, represent optionally halogen-substituted $C_3$-$C_8$-cycloalkyl or represent a group of the formula $M^1$-$Q_k$ in which $M^1$ represents optionally substituted alkylene, alkenylene or alkynylene, Q represents hydrogen, halogen, cyano, nitro, haloalkyl, in each case optionally substituted $C_3$-$C_8$-cycloalkyl, alkylcarbonyl or alkoxycarbonyl, in each case optionally substituted phenyl, hetaryl or represents a group T-$Re^4$, in which T represents —O—, —S(O)$_m$— or

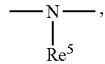

$Re^4$ represents hydrogen, in each case optionally substituted alkyl, alkenyl, alkynyl, cycloalkyl, cycloalkylalkyl, alkoxyalkyl, alkylcarbonyl, alkoxycarbonyl, phenyl, phenylalkyl, phenylalkoxy, hetaryl, hetarylalkyl, $Re^5$ represents hydrogen, represents in each case optionally substituted alkylcarbonyl, alkoxy-carbonyl, phenylcarbonyl or phenylalkoxycarbonyl, k represents the numbers 1 to 4, m represents the numbers 0 to 2, $Re^1$ and $Re^2$ together form an optionally substituted four- to seven-membered ring which may optionally be interrupted by heteroatoms, $L^1$ and $L^3$ independently of one another represent hydrogen, halogen, cyano or in each case optionally substituted alkyl, alkoxy, alk-S(O)$_m$—, phenyl, phenoxy or hetaryloxy, $L^2$ represents hydrogen, halogen, cyano, in each case optionally substituted alkyl, alkenyl, alkynyl, haloalkyl, cycloalkyl, phenyl, hetaryl or represents the group $M^2$-$Re^6$, in which $M^2$ represents —O— or —S(O)$_m$—, and $Re^6$ represents in each case optionally substituted alkyl, alkenyl, alkynyl, cycloalkyl, phenyl or hetaryl, $L^1$ and $L^3$ or $L^1$ and $L^2$ together form an optionally substituted five- or six-membered ring which may optionally be interrupted by heteroatoms.

Preferred are compounds of the formula (II), in which

K preferably represents fluorine, chlorine, bromine, iodine, cyano, $C_1$-$C_6$-alkyl, $C_1$-$C_6$-haloalkyl, $C_1$-$C_6$-alkoxy or $C_1$-$C_6$-haloalkoxy, $Re^1$, $Re^2$ and $Re^3$ each independently of one another preferably represent hydrogen, cyano, represent optionally halogen-substituted $C_3$-$C_6$-cycloalkyl or represent a group of the formula $M^1$-$Q_k$ in which $M^1$ preferably represents $C_1$-$C_8$-alkylene, $C_3$-$C_6$-alkenylene or $C_3$-$C_6$-alkynylene, Q preferably represents hydrogen, halogen, cyano, nitro, haloalkyl or represents optionally fluorine-, chlorine-, $C_1$-$C_6$-alkyl- or $C_1$-$C_6$-alkoxy-substituted $C_3$-$C_8$-cycloalkyl in which optionally one or two not directly adjacent ring members are replaced by oxygen and/or sulphur or represents in each case optionally halogen-substituted $C_1$-$C_6$-alkylcarbonyl or $C_1$-$C_6$-alkoxycarbonyl or represents in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl or hetaryl having 5 or 6 ring atoms (for example furanyl, pyridyl, imidazolyl, triazolyl, pyrazolyl, pyrimidyl, thiazolyl or thienyl) or represents a group T-$Re^4$, in which T preferably represents —O—, —S(O)$_m$— or

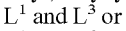

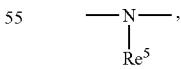

$Re^4$ preferably represents hydrogen, represents in each case optionally fluorine- and/or chlorine-substituted $C_1$-$C_8$-alkyl, $C_3$-$C_8$-alkenyl, $C_3$-$C_8$-alkynyl, $C_3$-$C_8$-cycloalkyl, $C_3$-$C_8$-cycloalkyl-$C_1$-$C_2$-alkyl, $C_1$-$C_6$-alkylcarbonyl, $C_1$-$C_6$-alkoxycarbonyl, represents phenyl, $C_1$-$C_4$-phenylalkyl, $C_1$-$C_4$-phenylalkyloxy, hetaryl or hetarylalkyl, hetaryl having 5 or 6 ring atoms, each of which radicals is optionally mono- to tetrasubstituted by halogen, $C_1$-$C_6$-alkyl, $C_1$-$C_6$-alkoxy, $C_1$-$C_4$-haloalkyl, $C_1$-$C_4$-haloalkoxy, nitro or cyano, $Re^5$ preferably represents hydrogen, represents in each case optionally fluorine- and/or chlorine-substituted $C_1$-$C_6$-alkylcarbonyl, $C_1$-$C_6$-alkoxycarbonyl, represents phenylcarbonyl or phenyl-$C_1$-$C_4$-alkyloxycarbonyl, each of which is optionally mono- to tetrasubstituted by halogen, $C_1$-$C_6$-alkyl, $C_1$-$C_6$-alkoxy, $C_1$-$C_4$-haloalkyl, $C_1$-$C_4$-haloalkoxy, nitro or cyano, k preferably represents the numbers 1 to 3, m preferably represents the numbers 0 to 2, $Re^1$ and $Re^2$ preferably form a five- or six-membered ring which may optionally be interrupted by an oxygen or sulphur atom, $L^1$ and $L^3$ independently of one another preferably represent hydrogen, cyano, fluorine, chlorine, bromine, iodine, $C_1$-$C_6$-alkyl, $C_1$-$C_4$-haloalkyl, $C_1$-$C_6$-alkoxy, $C_1$-$C_4$-haloalkoxy, $C_1$-$C_4$-alkyl-$S(O)_m$—, $C_1$-$C_4$-haloalkyl-$S(O)_m$—, represent phenyl, phenoxy, pyridinyloxy, thiazolyloxy or pyrimidyloxy, each of which is optionally mono- to trisubstituted by fluorine, chlorine, bromine, $C_1$-$C_6$-alkyl, $C_1$-$C_6$-alkoxy, $C_1$-$C_4$-haloalkyl, $C_1$-$C_4$-haloalkoxy, cyano or nitro, $L^2$ preferably represents hydrogen, fluorine, chlorine, bromine, iodine, cyano, represents in each case optionally fluorine- and/or chlorine-substituted $C_1$-$C_{10}$-alkyl, $C_2$-$C_{10}$-alkenyl, $C_2$-$C_6$-alkynyl, represents in each case optionally fluorine-, chlorine-substituted $C_3$-$C_6$-cycloalkyl, represents phenyl, pyridyl, thienyl, pyrimidyl or thiazolyl, each of which is optionally mono- to trisubstituted by fluorine, chlorine, bromine, $C_1$-$C_6$-alkyl, $C_1$-$C_6$-alkoxy, $C_1$-$C_4$-haloalkyl, $C_1$-$C_4$-haloalkoxy, cyano or nitro, or represents a group $M^2$-$R^6$ in which $M^2$ preferably represents —O— or —$S(O)_m$— and $Re^6$ preferably represents in each case optionally fluorine- and/or chlorine-substituted $C_1$-$C_8$-alkyl, $C_2$-$C_8$-alkenyl, $C_3$-$C_6$-alkynyl or $C_3$-$C_6$-cycloalkyl, represents phenyl, pyridyl, pyrimidyl or thiazolyl, each of which is optionally mono- to trisubstituted by fluorine, chlorine, bromine, $C_1$-$C_6$-alkyl, $C_1$-$C_6$-alkoxy, $C_1$-$C_4$-haloalkyl, $C_1$-$C_4$-haloalkoxy, cyano or nitro, $L^1$ and $L^3$ or $L^2$ and $L^3$ together preferably form an in each case optionally fluorine- and/or $C_1$-$C_2$-alkyl-substituted five- or six-membered ring which may optionally be interrupted by one or two oxygen atoms.

Particularly preferred are compounds of the formula II, in which

K particularly preferably represents chlorine, bromine or iodine, $Re^1$, $Re^2$ and $Re^3$ each independently of one another particularly preferably represent hydrogen or represent a group of the formula $M^1$-$Q_k$ in which $M^1$ particularly preferably represents $C_1$-$C_8$-alkylene, $C_3$-$C_6$-alkenylene or $C_3$-$C_6$-alkynylene, Q particularly preferably represents hydrogen, fluorine, chlorine, cyano, trifluoromethyl, $C_3$-$C_6$-cycloalkyl or represents a group T-$Re^4$, in which T particularly preferably represents —O— or —$S(O)_m$—, $Re^4$ particularly preferably represents hydrogen, represents $C_1$-$C_6$-alkyl, $C_3$-$C_6$-alkenyl, $C_3$-$C_6$-alkynyl or $C_3$-$C_6$-cycloalkyl, each of which is optionally mono- to trisubstituted by fluorine and/or chlorine, k particularly preferably represents the numbers 1 to 3, m particularly preferably represents the numbers 0 to 2, $L^1$ and $L^3$ independently of one another particularly preferably represent hydrogen, fluorine, chlorine, bromine, iodine, cyano, $C_1$-$C_4$-alkyl, $C_1$-$C_2$-haloalkyl, $C_1$-$C_4$-alkoxy, $C_1$-$C_2$-haloalkoxy, represent phenyl or phenoxy, each of which is optionally mono- or disubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, cyano or nitro, $L^2$ particularly preferably represents hydrogen, fluorine, chlorine, bromine, iodine, cyano, represents $C_1$-$C_6$-alkyl, $C_2$-$C_6$-alkenyl, $C_2$-$C_6$-alkynyl, $C_3$-$C_6$-cycloalkyl, each of which is optionally mono- to tridecasubstituted by fluorine and/or chlorine, or represents a group $M^2$-$Re^6$ in which $M^2$ particularly preferably represents —O— or —$S(O)_m$—, and $Re^6$ particularly preferably represents $C_1$-$C_6$-alkyl, $C_2$-$C_6$-alkenyl, $C_2$-$C_6$-alkynyl or $C_3$-$C_6$-cycloalkyl, each of which is optionally mono- to tridecasubstituted by fluorine and/or chlorine, represents phenyl or pyridyl, each of which is optionally mono- or disubstituted by fluorine, chlorine, bromine, $C_1$-$C_4$-alkyl, $C_1$-$C_4$-alkoxy, trifluoromethyl, difluoromethoxy, trifluoromethoxy, cyano or nitro.

Very particularly preferred are compounds of the formula (II), in which

K very particularly preferably represents iodine, $Re^1$ and $Re^2$ very particularly preferably represent hydrogen, $Re^3$ very particularly preferably represents a group of the formula $M^1$-Q in which $M^1$ very particularly preferably represents —CHCH$_3$—CH$_2$—, —C(CH$_3$)$_2$—CH$_2$—, —CHC$_2$H$_5$—CH$_2$—,

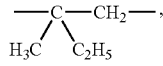

—C(C$_2$H$_5$)$_2$—CH$_2$—,

Q very particularly preferably represents hydrogen, fluorine, chlorine, cyano, trifluoromethyl, $C_3$-$C_6$-cycloalkyl or represents a group T-$Re^4$, in which T very particularly preferably represents —S—, —SO— or —SO$_2$—, $Re^4$ very particularly preferably represents methyl, ethyl, n-propyl, isopropyl, n-butyl, isobutyl, sec-butyl or tert-butyl, allyl, butenyl or isoprenyl, each of which is optionally mono- to trisubstituted by fluorine and/or chlorine, $L^1$ and $L^3$ independently of one another very particularly preferably represent hydrogen, fluorine, chlorine, bromine, iodine, cyano, methyl, ethyl, n-propyl, isopropyl, tert-butyl, methoxy, ethoxy, trifluormethyl, difluoromethoxy or trifluoromethoxy, $L^2$ very particularly preferably represents hydrogen, fluorine, chlorine, bromine, iodine, cyano, represents methyl, ethyl, n-propyl, isopropyl, n-butyl, isobutyl, sec-butyl, tert-butyl, allyl, butenyl or isoprenyl, each of which is optionally mono- to nonasubstituted by fluorine and/or chlorine, or represents a group $M^2$-$Re^6$, $M^2$ very particularly preferably represents oxygen or sulphur, and $Re^6$ very particularly preferably represents methyl, ethyl, n-propyl, isopropyl, n-butyl, isobutyl, sec-butyl, tert-butyl, allyl, butenyl or isoprenyl, each of which is optionally mono- to nonasubstituted by fluorine and/or chlorine, represents phenyl which is optionally mono- or disubstituted by fluorine, chlorine, bromine, methyl, ethyl, methoxy, trifluoromethyl, difluoromethoxy, trifluoromethoxy, cyano or nitro.

Especially preferred is the compound of the formula II-1

Surprisingly, the insecticidal and/or acaricidal action of the active compound combinations according to the invention is considerably higher than the sum of the actions of the individual active compounds. Thus, an unforeseeable true synergistic effect is present, and not just an addition of actions.

In addition to at least one active compound of the formula (I), the active compound combinations according to the invention comprise at least one active compound of the formula (II).

Preference is given to active compound combinations comprising compounds of the formula (I), in which X represents $C_1$-$C_4$-alkyl, bromine, $C_1$-$C_4$-alkoxy or $C_1$-$C_3$-haloalkyl, Y represents hydrogen, $C_1$-$C_4$-alkyl, fluorine, chlorine, bromine, $C_1$-$C_4$-alkoxy, $C_1$-$C_3$-haloalkyl, Z represents $C_1$-$C_4$-alkyl, chlorine, bromine, $C_1$-$C_4$-alkoxy, n represents a number from 0 to 2, A represents hydrogen or represents $C_1$-$C_6$-alkyl, $C_2$-$C_6$-alkenyl, $C_1$-$C_4$-alkoxy-$C_1$-$C_2$-alkyl, cycloalkyl having 3 to 8 ring atoms which may optionally be interrupted by oxygen and/or sulphur, each of which radicals is optionally mono- to trisubstituted by fluorine, or represents phenyl or benzyl, each of which is optionally mono- or disubtituted by fluorine, chlorine, bromine, $C_1$-$C_2$-alkyl, $C_1$-$C_2$-haloalkyl, $C_1$-$C_2$-alkoxy, $C_1$-$C_2$-haloalkoxy, nitro, B represents hydrogen, $C_1$-$C_2$-alkyl or $C_1$-$C_2$-alkoxy-$C_1$-$C_2$-alkyl or in which A and B together with the carbon atom to which they are attached form a saturated or unsaturated 3- to 7-membered ring which is optionally interrupted by oxygen and/or sulphur and is optionally mono- or disubstituted by fluorine, chlorine, $C_1$-$C_4$-alkyl, $C_1$-$C_4$-alkoxy, $C_1$-$C_2$-haloalkyl, $C_1$-$C_2$-haloalkoxy or $C_1$-$C_2$-alkylthio, G represents hydrogen (a) or represents the groups (b)
—CO—$R^1$ (c)
—C(O)—O—$R^2$ (d)
—$SO_2$—$R^3$ (e)
—P(O)($R^4$)($R^5$) or (f)
—C(O)—N($R^6$)($R^7$), in which $R^1$ represents $C_1$-$C_{16}$-alkyl, $C_2$-$C_{16}$-alkenyl, $C_1$-$C_4$-alkoxy-$C_1$-$C_4$-alkyl, $C_1$-$C_4$-alkylthio-$C_1$-$C_4$-alkyl or cycloalkyl having 3 to 6 ring atoms which may be interrupted by oxygen and/or sulphur atoms, each of which radicals is optionally mono- to pentasubstituted by fluorine or chlorine,
represents phenyl which is optionally mono- or disubstituted by fluorine, chlorine, bromine, nitro, $C_1$-$C_4$-alkyl, $C_1$-$C_4$-alkoxy, $C_1$-$C_4$-haloalkyl, $C_1$-$C_4$-halogenalkoxy,
represents benzyl which is optionally mono- or disubstituted by fluorine, chlorine, bromine, $C_1$-$C_4$-alkyl, $C_1$-$C_4$-alkoxy, $C_1$-$C_4$-haloalkyl, $C_1$-$C_4$-haloalkoxy,
represents pyridyl, pyrimidyl, thiazolyl or pyrazolyl, each of which is optionally mono- or disubstituted by chlorine, bromine and/or $C_1$-$C_4$-alkyl, $R^2$ represents $C_1$-$C_{20}$-alkyl, $C_2$-$C_{20}$-alkenyl, $C_1$-$C_6$-alkoxy-$C_2$-$C_6$-alkyl, $C_1$-$C_6$-polyalkoxy-$C_2$-$C_6$-alkyl, each of which is optionally mono- to pentasubstituted by fluorine or chlorine,
represents phenyl or benzyl, each of which is optionally mono- or disubstituted by fluorine, chlorine, bromine, nitro, $C_1$-$C_6$-alkyl, $C_1$-$C_6$-alkoxy, $C_1$-$C_4$-haloalkyl, $R^3$ represents $C_1$-$C_4$-alkyl which is optionally mono- to pentasubstituted by fluorine or chlorine, represents phenyl or benzyl, each of which is optionally mono- or disubstituted by $C_1$-$C_4$-alkyl, fluorine, chlorine, bromine, $C_1$-$C_4$-haloalkyl, $C_1$-$C_4$-alkoxy, $C_1$-$C_4$-haloalkoxy, nitro or cyano, $R^4$ and $R^5$ independently of one another represent $C_1$-$C_4$-alkyl, $C_1$-$C_4$-alkoxy, $C_1$-$C_4$-alkyl-amino, di-($C_1$-$C_4$)-alkylamino, $C_1$-$C_4$-alkylthio, $C_2$-$C_4$-alkenylthio, $C_3$-$C_6$-cycloalkylthio, each of which is optionally mono- to trisubstituted by fluorine or chlorine, represent phenyl, phenoxy or phenylthio, each of which is optionally mono- or disubstituted by fluorine, chlorine, bromine, nitro, cyano, $C_1$-$C_2$-alkoxy, $C_1$-$C_2$-haloalkoxy, $C_1$-$C_2$-alkylthio, $C_1$-$C_2$-haloalkylthio, $C_1$-$C_2$-alkyl, $C_1$-$C_2$-haloalkyl, $R^6$ and $R^7$ independently of one another represent $C_1$-$C_6$-alkyl, $C_1$-$C_6$-alkoxy, $C_3$-$C_6$-alkenyl, $C_1$-$C_4$-alkoxy-$C_1$-$C_2$-alkyl, each of which is optionally mono- to trisubstituted by fluorine or chlorine, represent benzyl which is optionally mono- or disubstituted by fluorine, chlorine, bromine, $C_1$-$C_2$- haloalkyl, $C_1$-$C_4$-alkyl or $C_1$-$C_4$-alkoxy or together represent a 5- or 6-membered ring which is optionally interrupted by oxygen or sulphur and which may optionally be substituted by $C_1$-$C_2$-alkyl, and at least one active compound of the formula (II).

In the halogen-containing radicals in the preferred ranges, halogen preferably represents chlorine and fluorine.

Particularly preferred are active compound combinations comprising compounds of the formula (I), in which X represents $C_1$-$C_4$-allyl, $C_1$-$C_4$-alkoxy or trifluoromethyl, Y represents hydrogen, $C_1$-$C_4$-alkyl, chlorine, bromine, $C_1$-$C_4$-alkoxy, $C_1$-$C_2$-haloalkyl, Z represents $C_1$-$C_4$-alkyl, chlorine, bromine, $C_1$-$C_4$-alkoxy, n represents 0 or 1, A and B together with the carbon atom to which they are attached form a saturated 5- or 6-membered ring which is optionally monosubstituted by $C_1$-$C_4$-alkyl or $C_1$-$C_4$-alkoxy, G represents hydrogen (a) or represents the groups —CO—$R^1$ (b)

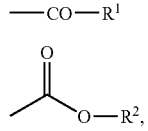

(c)

in which $R^1$ represents $C_1$-$C_{12}$-alkyl, $C_2$-$C_{12}$-alkenyl, $C_1$-$C_4$-alkoxy-$C_1$-$C_2$-alkyl or cycloalkyl having 3 to 6 ring atoms which may be interrupted by 1 or 2 oxygen atoms, each of which radicals is optionally mono- to trisubstituted by fluorine or chlorine, or represents phenyl which is optionally monosubstituted by fluorine, chlorine, bromine, nitro, $C_1$-$C_4$-alkyl, $C_1$-$C_4$-alkoxy, trifluoromethyl or trifluoromethoxy;

$R^2$ represents $C_1$-$C_{12}$-alkyl, $C_2$-$C_{12}$-alkenyl, $C_1$-$C_4$-alkoxy-$C_2$-$C_4$-alkyl, represents phenyl or benzyl, each of which is optionally monosubstituted by fluorine, chlorine, bromine, nitro, $C_1$-$C_4$-alkyl, $C_1$-$C_4$-alkoxy or trifluoromethyl, and at least one active compound of the formula (II).

Very particularly preferred are active compound combinations comprising compounds of the formula (I), in which X represents methyl, ethyl, methoxy, ethoxy or trifluoromethyl, Y represents hydrogen, methyl, ethyl, chlorine, bromine, methoxy or trifluoromethyl, Z represents methyl, ethyl, chlorine, bromine or methoxy, n represents 0 or 1, A and B together with the carbon atom to which they are attached form a saturated 5- or 6-membered ring which is optionally monosubstituted by methyl, ethyl, propyl, methoxy, ethoxy, propoxy, butoxy or isobutoxy, G represents hydrogen (a) or represents the groups —CO—$R^1$ (b)

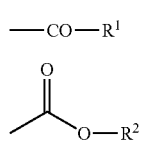

(c)

in which $R^1$ represents $C_1$-$C_8$-alkyl, $C_2$-$C_8$-alkenyl, $C_1$-$C_3$-alkoxy-$C_1$-$C_2$-alkyl or cycloalkyl having 3 to 6 ring atoms which may be interrupted by 1 or 2 oxygen atoms, each of which radicals are optionally mono- to trisubstituted by fluorine or chlorine, represents phenyl which is optionally monosubstituted by fluorine, chlorine, bromine, methyl, methoxy, trifluoromethyl or trifluoromethoxy;

$R^2$ represents $C_1$-$C_8$-alkyl, $C_2$-$C_8$-alkenyl, $C_1$-$C_4$-alkoxy-$C_2$-$C_3$-alkyl, represents phenyl or benzyl, each of which is optionally monosubstituted by fluorine, chlorine, bromine, nitro, methyl, methoxy or trifluoromethyl, and at least one active compound of the formula (II).

Especially preferred are active compound combinations comprising the compound of the formula (I-b-1)

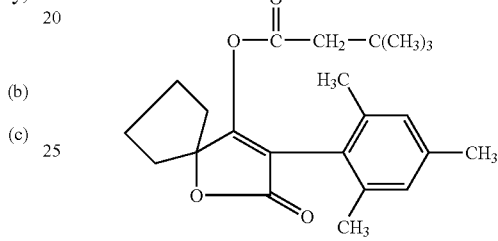

(I-b-1)

and at least one active compound of the formula (II).

Emphasis is given to active compound combinations comprising the compound of the formula (I-b-1) and the active compound of the formula (II-1).

The general or preferred radical definitions or illustrations given above can be combined with one another as desired, i.e. including combinations between the respective ranges and preferred ranges. The definitions apply both to the end product and, correspondingly, to precursors and intermediates.

Preference according to the invention is given to the compounds of the formulae (I) and (II) which contain a combination of the meanings given above as being preferred (preferable).

Particular preference according to the invention is given to the compounds of the formulae (I) and (II) which contain a combination of the meanings given above as being particularly preferred.

Very particular preference according to the invention is given to the compounds of the formulae (I) and (II) which contain a combination of the meanings given above as being very particularly preferred.

Saturated or unsaturated hydrocarbon radicals, such as alkyl or alkenyl, can in each case be straight-chain or branched, including in combination with heteroatoms, such as, for example, in alkoxy.

Unless indicated otherwise, optionally substituted radicals can be mono- or polysubstituted, where in the case of polysubstitutions the substituents can be identical or different.

In addition, the active compound combinations can also comprise further fungicidally, acaricidally or insecticidally active mixing partners.

If the active compounds in the active compound combinations according to the invention are present in certain weight ratios, the synergistic effect is particularly pronounced. However, the weight ratios of the active compounds in the active compound combinations can be varied within a relatively wide range. In general, the combinations according to the invention comprise active compounds of the formula (I) and the mixing partner of the formula (II) in the preferred and particularly preferred mixing ratios stated below:

The preferred mixing ratio is 500:1 to 1:50.

The particularly preferred mixing ratio is 25:1 to 1:10.

The mixing ratios are based on weight ratios. The ratio is to be understood as meaning active compound of the formula (I): mixing partner of the formula (II).

The active compound combinations according to the invention are suitable for controlling animal pests, preferably arthropods and nematodes, in particular insects and arachnids, found in agriculture, in animal health, in forests, in gardens and leisure facilities, in the protection of stored products and materials and in the hygiene sector, while exhibiting good tolerability to plants, low toxicity to warm-blooded species and good environmental compatibility. They are active against normally sensitive and resistant species, and against all or individual developmental stages. The above-mentioned pests include:

From the order of the Isopoda, for example, *Oniscus asellus, Armadillidium vulgare, Porcellio scaber.*

From the order of the Diplopoda, for example, *Blaniulus guttulatus.*

From the order of the Chilopoda, for example, *Geophilus carpophagus, Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp., *Schistocerca gregaria.*

From the order of the Blattaria, for example, *Blatta orientalis, Periplaneta americana, Leucophaea maderae, Blattella germanica.*

From the order of the *Dermaptera*, for example, *Forficula auricularia.*

From the order of the *Isoptera*, for example, *Reticulitermes* spp.

From the order of the Phthiraptera, for example, *Pediculus humanus corporis, Haematopinus* spp., *Linognathus* spp., *Trichodectes* spp., *Damalinia* spp.

From the order of the Thysanoptera, for example, *Hercinothrips femoralis, Thrips tabaci, Thrips palmi, Frankliniella occidentalis.*

From the order of the Heteroptera, for example, *Eurygaster* spp., *Dysdercus intermedius, Piesma quadrata, Cimex lectularius, Rhodnius prolixus, Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium comi, Saissetia oleae, Laodelphax striatellus, Nilaparvata lugens, Aonidiella aurantii, Aspidiotus hederae, Pseudococcus* spp., *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofinannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order of the Coleoptera, for example, *Anobium punctatum, Rhizopertha doniinica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Lissorhoptrus oryzophilus.*

From the order of the *Hymenoptera*, for example, *Diprion* spp., *Hoplocampa* spp., *Lasius* spp., *Monomorium pharaonis, Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp., *Liriomyza* spp.

From the order of the Siphonaptera, for example, *Xenopsylla cheopis, Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp. *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* ssp., *Hemitarsonemus* ssp., *Brevipalpus* ssp.

The plant-parasitic nematodes include, for example, *Pratylenchus* ssp., *Radopholus similis, Ditylenchus dipsaci, Tylenchulus semipenetrans, Heterodera* ssp., *Globodera* ssp., *Meloidogyne* spp., *Aphelenchoides* ssp., *Longidorus* ssp., *Xiphinema* ssp., *Trichodorus* ssp., *Bursaphelenchus* spp.

The active compound combinations according to the invention of compounds of the formula (I) and at least one compound of the formula (II) are particularly suitable for controlling "biting" pests. These include in particular the following pests:

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* ssp., *Bucculatrix thurberiella, Phylloc-nistis citrella, Agrotis* ssp., *Euxoa* ssp., *Feltia* ssp., *Earias insulana, Heliothis* ssp., *Mamestra brassicae, Panolis flammea, Spodoptera* ssp., *Trichoplusia ni, Carpocapsa pomonella, Pieris* ssp., *Chilo* ssp., *Pyrausta nubilalis, Ephestia kuehniella, Galleria mellonella, Tineola bisselliella, Tinea pellionella, Hofinannophila pseudospretella, Cacoecia podana, Capua reticulana, Choristoneura fumliferana, Clysia ambiguella, Homona magnanima, Tortrix viridana, Cnaphalocerus* ssp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* ssp., *Psylliodes chrysocephala, Epilachna varivestis, Atomaria* ssp., *Oryzaephilus surinamensis, Anthonomus* ssp., *Sitophilus* ssp., *Otiorrhynchus sulcatus,*

*Cosmopolites sordidus, Ceuthorrhynchus assimilis, Hypera postica, Dermestes* ssp., *Trogoderna* ssp., *Anthrenus* ssp., *Attagenus* ssp., *Lyctus* ssp., *Meligethes aeneus, Ptinus* ssp., *Niptus hololeucus, Gibbium psylloides, Tribolium* ssp., *Tenebrio molitor, Agriotes* ssp., *Conoderus* ssp., *Melolontha melolontha, Amphimallon solstitialis, Costelytra zealandica, Lissorhoptrus oryzophilus*.

The active compound combinations according to the invention of compounds of the formula (I) and at least one compound of the formula (II) are additionally particularly suitable for controlling "sucking" pests. These include, in particular, the following pests:

From the order of the *Homoptera*, for example, *Aleurodes brassicae, Bemisia tabaci, Trialeurodes vaporariorum, Aphis gossypii, Brevicoryne brassicae, Cryptomyzus ribis, Aphis fabae, Aphis pori, Eriosoma lanigerum, Hyalopterus arundinis, Phylloxera vastatrix, Pemphigus* ssp., *Macrosiphum avenae, Myzus* ssp., *Phorodon humuli, Rhopalosiphum padi, Empoasca* ssp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* ssp., *Psylla* ssp.

The active compound combinations according to the invention are particularly distinguished by excellent action against caterpillars, beetle larvae, spider mites, aphids and leaf-mining flies.

The active compound combinations can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are:

for example ammonium salts and ground natural minerals such as kaolins, clays, talc, chalk, quartz, attapulgite, montmorillonite or diatomaceous earth, and ground synthetic materials such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic colorants such alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The active compound combinations according to the invention can be present in their commercially available formulations and in the use forms, prepared from these formulations, as a mixture with other active compounds, such as insecticides, attractants, sterilants, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Mixtures with other known active compounds such as herbicides or with fertilizers and growth regulators are also possible.

When used as insecticides, the active compound combinations according to the invention can furthermore be present in their commercially available formulations and in the use forms, prepared from these formulations, as a mixture with synergists. Synergists are compounds which increase the action of the active compounds, without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and stored-product pests, the active compound combinations are distinguished by an excellent residual action on wood and clay as well as good stability to alkali on limed substrates.

The active compound combinations according to the invention are not only active against plant pests, hygiene pests and stored-product pests, but also, in the veterinary medicine sector, against animal parasites (ectoparasites) such as hard ticks, soft ticks, mange mites, harvest mites, flies (stinging and licking), parasitizing fly larvae, lice, head lice, bird lice and fleas. These parasites include:

From the order of the Anoplurida, for example, *Haematopinus* ssp., *Linognathus* ssp., *Pediculus* spp., *Phtirus* ssp., *Solenopotes* ssp.

From the order of the Mallophagida and the suborders Amblycerina and Ischnocerina, for example, *Trimenopon* ssp., *Menopon* ssp., *Trinoton* ssp., *Bovicola* ssp., *Wemeckiella* ssp., *Lepikentron* spp., *Damalina* ssp., *Trichodectes* ssp., *Felicola* ssp.

From the order Diptera and the suborders Nematocerina and Brachycerina, for example, *Aedes* spp., *Anopheles* ssp., *Culex* ssp., *Simulium* ssp., *Eusimulium* ssp., *Phlebotomus* ssp., *Lutzomyia* spp., *Culicoides* ssp., *Chrysops* ssp., *Hybornitra* ssp., *Atylotus* ssp., *Tabanus* ssp., *Haematopota* spp., *Philipomyia* ssp., *Braula* ssp., *Musca* ssp., *Hydrotaea* ssp., *Stomoxys* ssp., *Haematobia* ssp., *Morellia* ssp., *Fannia* ssp., *Glossina* ssp., *Calliphora* ssp., *Lucilia* ssp., *Chrysomyia* ssp., *Wohlfahrtia* ssp., *Sarcophaga* ssp., *Oestrus* ssp., *Hypoderma* ssp., *Gasterophilus* ssp., *Hippobosca* spp., *Lipoptena* ssp., *Melophagus* ssp.

From the order of the Siphonapterida, for example, *Pulex* ssp., *Ctenocephalides* ssp., *Xenopsylla* spp., *Ceratophyllus* ssp.

From the order of the Heteropterida, for example, *Cimex* ssp., *Triatoma* ssp., *Rhodnius* ssp., *Panstrongylus* ssp.

From the order of the Blattarida, for example, *Blatta orientalis, Periplaneta americana, Blattella germanica, Supella* ssp.

From the subclass of the Acaria (Acarida) and the orders of the Meta- and Mesostigmata, for example, *Argas* ssp., *Ornithodorus* ssp., *Otobius* ssp., *Ixodes* ssp., *Amblyomma* ssp., *Boophilus* spp., *Dermacentor* ssp., *Haemophysalis* ssp., *Hyalomma* ssp., *Rhipicephalus* ssp., *Dermanyssus* spp., *Raillietia* ssp., *Pneumonyssus* ssp., *Sternostoma* ssp., *Varroa* ssp.

From the order of the Actinedida (Prostigmata) and Acaridida (Astigmata), for example, *Acarapis* spp., *Cheyletiella* ssp., *Ornithocheyletia* ssp., *Myobia* ssp., *Psorergates* ssp., *Demodex* ssp., *Trombicula* ssp., *Listrophorus* ssp., *Acarus* ssp., *Tyrophagus* ssp., *Caloglyphus* ssp., *Hypodectes* spp., *Pterolichus* ssp., *Psoroptes* ssp., *Chorioptes* ssp., *Otodectes* ssp., *Sarcoptes* ssp., *Notoedres* spp., *Knemidocoptes* ssp., *Cytodites* ssp., *Laminosioptes* ssp.

The active compound combinations according to the invention are also suitable for controlling arthropods which attack agricultural livestock such as, for example, cattle, sheep, goats, horses, pigs, donkeys, camels, buffaloes, rabbits, chickens, turkeys, ducks, geese, honey-bees, other domestic animals such as, for example, dogs, cats, caged birds, aquarium fish and so-called experimental animals such as, for example, hamsters, guinea pigs, rats and mice. By controlling these arthropods, cases of death and reductions in productivity (for meat, milk, wool, hides, eggs, honey and the like) should be diminished, so that more economical and simpler animal husbandry is possible by the use of the active compound combinations according to the invention.

The active compound combinations according to the invention are used in the veterinary sector in a known manner by enteral administration in the form of, for example, tablets, capsules, potions, drenches, granules, pastes, boluses, the feed-through method, suppositories, by parenteral administration such as, for example, by injections (intramuscularly, subcutaneously, intravenously, intraperitoneally and the like), implants, by nasal administration, by dermal administration in the form of, for example, immersing or dipping, spraying, pouring-on, spotting-on, washing, dusting, and with the aid of active-compound-containing moulded articles such as collars, ear tags, tail tags, limb bands, halters, marking devices and the like.

When used for cattle, poultry, domestic animals and the like, the active compound combinations can be applied as formulations (for example powders, emulsions, flowables) comprising the active compounds in an amount of 1 to 80% by weight, either directly or after 100- to 10 000-fold dilution, or they may be used as a chemical dip.

Moreover, it has been found that the active compound combinations according to the invention show a potent insecticidal action against insects which destroy industrial materials.

The following insects may be mentioned by way of example and with preference, but not by way of limitation:

Beetles such as

*Hylotrupes bajulus, Chlorophorus pilosis, Anobium punctatum, Xestobium rufovillosum, Ptilinus pecticomis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Dermapterans such as

*Sirex juvencus, Urocerus gigas, Urocerus gigas taignus, Urocerus augur.*

Termites such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristle-tails such as *Lepisma saccharina.*

Industrial materials in the present context are understood as meaning non-living materials such as, preferably, polymers, adhesives, glues, paper and board, leather, wood, timber products and paints.

The material which is to be protected from insect attack is very particularly preferably wood and timber products.

Wood and timber products which can be protected by the composition according to the invention, or mixtures comprising it, are to be understood as meaning, for example:

Construction timber, wooden beams, railway sleepers, bridge components, jetties, vehicles made of wood, boxes, pallets, containers, telephone poles, wood panelling, windows and doors made of wood, plywood, chipboard, joinery, or timber products which quite generally are used in house construction or building joinery.

The active compound combinations can be used as such, in the form of concentrates or generally customary formulations such as powders, granules, solutions, suspensions, emulsions or pastes.

The abovementioned formulations can be prepared in a manner known per se, for example by mixing the active compounds with at least one solvent or diluent, emulsifier, dispersant and/or binder or fixative, water repellant, if desired desiccants and UV stabilizers, and if desired colorants and pigments and other processing auxiliaries.

The insecticidal compositions or concentrates used for protecting wood and timber products comprise the active compound according to the invention in a concentration of 0.0001 to 95% by weight, in particular 0.001 to 60% by weight.

The amount of composition or concentrate employed depends on the species and the abundance of the insects and on the medium. The optimal quantity to be employed can be determined in each case by test series upon application. In general, however, it will suffice to employ 0.0001 to 20% by weight, preferably 0.001 to 10% by weight, of the active compound, based on the material to be protected.

A suitable solvent and/or diluent is an organochemical solvent or solvent mixture and/or an oily or oil-type organochemical solvent or solvent mixture of low volatility and/or a polar organochemical solvent or solvent mixture and/or water and, if appropriate, an emulsifier and/or wetter.

Organochemical solvents which are preferably employed are oily or oil-type solvents with an evaporation number of above 35 and a flash point of above 30° C., preferably above 45° C. Such involatile, water-insoluble, oily and oil-type solvents which are used are suitable mineral oils or their aromatic fractions or mineral oil-containing solvent mixtures, preferably white spirit, petroleum and/or alkylbenzene.

Mineral oils with a boiling range of 170 to 220° C., white spirit with a boiling range of 170 to 220° C., spindle oil with a boiling range of 250 to 350° C., petroleum and aromatics with a boiling range of 160 to 280° C., oil of turpentine, and the like are advantageously used.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility and with an evaporation number of above 35 and a flash point of above 30° C., preferably above 45° C., can be replaced in part by organochemical solvents of high or medium volatility, with the proviso that the solvent mixture also has an evaporation number of above 35 and a flash point of above 30° C., preferably above 45° C., and that the mixture is soluble or emulsifiable in this solvent mixture.

In a preferred embodiment, some of the organochemical solvent or solvent mixture or an aliphatic polar organochemical solvent or solvent mixture is replaced. Aliphatic organochemical solvents which contain hydroxyl and/or ester and/or ether groups are preferably used, such as, for example, glycol ethers, esters or the like.

Organochemical binders used for the purposes of the present invention are the synthetic resins and/or binding drying oils which are known per se and which can be diluted in water and/or dissolved or dispersed or emulsified in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable and/or drying oils and/or physically drying binders based on a natural and/or synthetic resin.

The synthetic resin employed as binder can be employed in the form of an emulsion, dispersion or solution. Bitumen or bituminous substances may also be used as binders, in amounts of up to 10% by weight. In addition, colorants, pigments, water repellants, odour-masking agents, and inhibitors or anticorrosive agents and the like, all of which are known per se, can be employed.

In accordance with the invention, the composition or the concentrate preferably comprises, as organochemical binders, at least one alkyd resin or modified alkyd resin and/or a drying vegetable oil. Alkyd resins which are preferably used in accordance with the invention are those with an oil content of over 45% by weight, preferably 50 to 68% by weight.

Some or all of the abovementioned binder can be replaced by a fixative (mixture) or plasticizer (mixture). These additives are intended to prevent volatilization of the active compounds, and also crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, phosphoric esters such as tributyl phosphate, adipic esters such as di(2-ethylhexyl) adipate, stearates such as butyl stearate or amyl stearate, oleates such as butyl oleate, glycerol ethers or higher-molecular-weight glycol ethers, glycerol esters and p-toluenesulphonic esters.

Fixatives are based chemically on polyvinyl alkyl ethers such as, for example, polyvinyl methyl ether, or ketones such as benzophenone and ethylenebenzophenone.

Other suitable solvents or diluents are, in particular, water, if appropriate as a mixture with one or more of the abovementioned organochemical solvents or diluents, emulsifiers and dispersants.

Particularly effective timber protection is achieved by industrial-scale impregnating processes, for example the vacuum, double-vacuum or pressure processes.

The active compound combinations according to the invention can equally be employed for protecting objects which come into contact with saltwater or brackish water, such as hulls, screens, nets, buildings, quaysides and signalling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent stops in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the active compound combinations according to the invention have an outstanding antifouling action.

Use of the active compound combinations according to the invention allows the use of heavy metals such as, for example, in bis(trialkyltin) sulphides, tri-n-butyltin laurate, tri-n-butyltin chloride, copper(I) oxide, triethyltin chloride, tri-n-butyl (2-phenyl-4-chlorophenoxy)tin, tributyltin oxide, molybdenum disulphide, antimony oxide, polymeric butyl titanate, phenyl(bispyridine)-bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylenebisthiocarbamate, zinc oxide, copper(I) ethylenebisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fingicides, herbicides, molluscicides, or other antifouling active compounds.

Preferable suitable components in combinations with the antifouling compositions according to the invention are:

algicides such as 2-tert-butyl-amino-4-cyclopropylamino-6-methylthio-1, 3,5-triazine, dichlorophen, diuron, endothal, fentin acetate, isoproturon, methabenzthiazuron, oxyfluorfen, quinoclamine and terbutryn;

fungicides such as benzo[b]thiophenecarboxylic acid cyclohexylamide S,S-dioxide, dichlofluanid, fluorfolpet, 3-iodo-2-propynyl butylcarbamate, tolylfluanid and azoles such as azaconazole, cyproconazole, epoxyconazole, hexaconazole, metconazole, propiconazole and tebuconazole;

molluscicides such as fentin acetate, metaldehyde, methiocarb, niclosamid, thiodicarb and trimethacarb;

or conventional antifouling active compounds such as 4,5-dichloro-2-octyl-4-isothiazolin-3-one, diiodomethylparatryl sulphone, 2-(N,N-dimethylthiocarbamoylthio)-5-nitrothiazyl, potassium salts, copper salts, sodium salts and zinc salts of 2-pyridinethiol 1-oxide, pyridine-triphenylborane, tetrabutyldistannoxane, 2,3,5,6-tetrachloro-4-(methylsulphonyl)pyridine, 2,4,5,6-tetrachloroisophthalonitrile, tetramethylthiuram disulphide and 2,4,6-trichlorophenylmaleimide.

The antifouling compositions used comprise the active compound combinations according to the invention in a concentration of 0.001 to 50% by weight, in particular 0.01 to 20% by weight.

Moreover, the antifouling compositions according to the invention comprise the customary components such as, for example, those described in Ungerer, *Chem. Ind.* 1985, 37, 730-732 and Williams, Antifouling Marine Coatings, Noyes, Park Ridge, 1973.

Besides the algicidal, fingicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compound combinations are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* ssp.

From the order of the Chilopoda, for example, *Geophilus* ssp.

From the order of the Zygentoma, for example, *Ctenolepisma* ssp., *Lepisma saccharina, Lepismodes inquilinus*.

From the order of the Blattaria, for example, *Blatta orientalies, Blattella germanica, Blattella asahinai, Leucophaea maderae, Panchlora* ssp., *Parcoblatta* ssp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the *Dermaptera*, for example, *Forficula auricularia*.

From the order of the *Isoptera*, for example, *Kalotermes* ssp., *Reticulitermes* ssp.

From the order of the Psocoptera, for example, *Lepinatus* ssp., *Liposcelis* ssp.

From the order of the Coleptera, for example, *Anthrenus* ssp., *Attagenus* ssp., *Dermestes* ssp., *Latheticus oryzae, Necrobia* ssp., *Ptinus* ssp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* ssp., *Calliphora erythrocephala, Chrysozona pluvialis, Culex quinquefasciatus, Culex pipiens, Culex tarsalis, Drosophila* ssp., *Fannia canicularis, Musca domestica, Phlebotomus* ssp., *Sarcophaga carnaria, Simulium* ssp., *Stomoxys calcitrans, Tipula paludosa*.

From the order of the *Lepidoptera*, for example, *Achroia grisella, Galleria mellonella, Plodia interpunctella, Tinea cloacella, Tinea pellionella, Tineola bisselliella*.

From the order of the *Siphonaptera*, for example, *Ctenocephalides canis, Ctenocephalides felis, Pulex irritans, Tunga penetrans, Xenopsylla cheopis*.

From the order of the *Hymenoptera*, for example, *Camponotus herculeanus, Lasius fuliginosus, Lasius niger, Lasius umbratus, Monomorium pharaonis, Paravespula* ssp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodnius prolixus, Triatoma infestans*.

They are used as aerosols, pressureless spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment according to the invention of the plants and parts of plants with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processibility of the harvested products are possible which exceed the effects which were actually to be expected.

The transgenic plants or plant cultivars (i.e. those obtained by genetic engineering) which are preferred and to be treated according to the invention include all plants which, in the genetic modification, received genetic material which imparts particularly advantageous useful traits to these plants. Examples of such traits are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processibility of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco oilseed rape and also fruit plants (with the fruits apples, pears, citrus fruits and grapes), and particular emphasis is given to maize, soya beans, potatoes, cotton, tobacco and oilseed rape. Traits that are particularly emphasized are the increased defence of the plants against insects, arachnids, nematodes and slugs and snails by toxins formed in the plants, in particular those formed by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits which are also particularly emphasized are the increased resistance of plants to fungi, bacteria and viruses by systemic acquired resistance (SAR), systemin, phytoalexins, elicitors and resistance genes and the correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes in question which impart the desired traits can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these or still-to-be-developed genetic traits, which plants will be developed and/or marketed in the future.

The plants listed can be treated according to the invention in a particularly advantageous manner with the active compound mixtures according to the invention. The preferred ranges stated above for the mixtures also apply to the treatment of these plants. Particular emphasis is given to the treatment of plants with the mixtures specifically mentioned in the present text.

The good insecticidal and acaricidal action of the active compound combinations according to the invention can be seen from the examples which follow. While the individual active compounds show weaknesses in their action, the combinations show an action which exceeds a simple sum of actions.

A synergistic effect in insecticides and acaricides is always present when the action of the active compound combinations exceeds the total of the actions of the active compounds when applied individually.

The expected action for a given combination of two active compounds can be calculated as follows, using the Colby formula (S. R. Colby, "Calculating Synergistic and Antagonistic Responses of Herbicide Combinations", Weeds 1967, 15, 20-22):

If

X is the kill rate, expressed as a percentage of the untreated control, when employing active compound A at an application rate of m g/ha or in a concentration of m ppm, Y is the kill rate, expressed as a percentage of the untreated control, when employing active compound B at an application rate of n g/ha or in a concentration of n ppm and E is the kill rate, expressed as a percentage of the untreated control, when employing active compounds A and B at application rates of m and n g/ha or in a concentration of m and n ppm, then $$E = X + Y - \frac{X \cdot Y}{100}$$

If the actual insecticidal kill rate exceeds the calculated value, the action of the combination is superadditive, i.e. a synergistic effect is present. In this case, the actually observed kill rate must exceed the value calculated using the above formula for the expected kill rate (E).

EXAMPLES

Example A

Phaedon Larvae Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed. The kill rates determined are calculated using the Colby formula (see page 32).

In this test, the following active compound combination in accordance with the present application has a synergistically enhanced activity, compared to the active compounds applied on their own:

TABLE A

| | Plant-damaging insects *Phaedon* larvae test | |
|---|---|---|
| Active compounds | Concentration of active compound in ppm | Kill rate in % after $6^d$ |
| Compound II-1 | 4 | 65 |
| Compound (I-b-1) | 100 | 30 |
| Compound II-1 + compound I-b-1 | 4 + 100 | found* 85    calc.** 75.5 |

*found = activity found
**calc. = activity calculated using the Colby formula

Example B

Spodoptera Frugiperda Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the army worm (*Spodoptera frugiperda*) while the leaves are still moist.

After the desired period of time, the kill in % is determined. 100% means that all caterpillars have been killed; 0% means that none of the caterpillars have been killed. The kill rates determined are calculated using the Colby formula (see page 32).

In this test, the following active compound combination in accordance with the present application has a synergistically enhanced activity, compared to the active compounds applied on their own:

TABLE B

| | Plant-damaging insects *Spodoptera frugiperda* test | |
|---|---|---|
| Active compounds | Concentration of active compound in ppm | Kill rate in % after $6^d$ |
| Compound II-1 | 0.16 | 85 |
| Compound (I-b-1) | 100 | 5 |
| Compound II-1 + Compound I-b-1 | 0.16 + 100 | found* 95    calc.** 85.75 |

*found = activity found
**calc. = activity calculated using the Colby formula

What is claimed is:

1. A composition comprising a compound of formula (II-1)

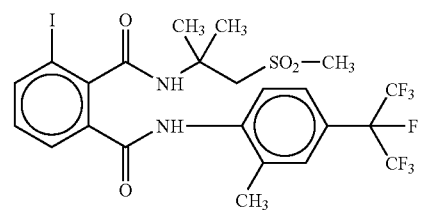

(II-1)

and a compound of formula (I-b-1)

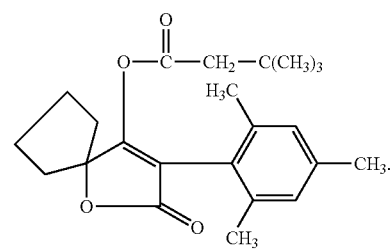

(I-b-1)

2. A method for controlling animal pests comprising allowing an effective amount of a composition according to claim 1 to act on animal pests and/or their habitat.

3. A process for preparing an insecticidal or acaridical composition comprising mixing a composition according to claim 1 with one or more extenders and/or surfactants.

* * * * *